(12) United States Patent
Mansilla

(10) Patent No.: US 7,482,030 B2
(45) Date of Patent: Jan. 27, 2009

(54) NATURAL HERB COMPOSITION FOR THE TREATMENT OF DIABETES AND MANUFACTURING METHOD THEREOF

(76) Inventor: Audino Mansilla, Perito Moreno 736 - Piso 1, Dto.6, San Martin de los Andes, Pcla. de Neuquén (AR)

( * ) Notice: Subject to any disclaimer, the term of this patent is extended or adjusted under 35 U.S.C. 154(b) by 61 days.

(21) Appl. No.: 11/809,747

(22) Filed: Jun. 1, 2007

(65) Prior Publication Data

US 2008/0299236 A1    Dec. 4, 2008

(51) Int. Cl.
*A01N 65/00* (2006.01)

(52) U.S. Cl. .................................................... 424/725
(58) Field of Classification Search ................... None
See application file for complete search history.

(56) References Cited

OTHER PUBLICATIONS

Soto, Agricultura Tecnica (Santiago), 1984, vol. 44, No. 3, pp. 195-198.*

* cited by examiner

*Primary Examiner*—Michael V Meller
(74) *Attorney, Agent, or Firm*—Evelyn A. Defilló; Defillo & Associates, Inc.

(57) ABSTRACT

The present invention refers to a new composition comprising natural herbs for the treatment of diabetes, and to a method for preparing said composition.

3 Claims, No Drawings

NATURAL HERB COMPOSITION FOR THE TREATMENT OF DIABETES AND MANUFACTURING METHOD THEREOF

FIELD OF THE INVENTION

The present invention pertains to the field of homeopathic medicine and specifically refers to a composition based on herbs for the treatment of diabetes and to a method for preparing said composition. The composition of the present invention comprises the herbs *Mulinum spinosum* and *Chamaemelum nobile* mixed in a defined proportion using mineral water as a solvent.

DESCRIPTION OF THE PRIOR ART

Neneo, whose scientific name is *Mulinum spinosum,* is a plant that belongs to the Apiaceae family.

Its most outstanding general features are a spiny shrub appearance, with a dome or cushion-like shape that may reach 1.2 meters in height. The leaves are trifid (split in three) and spinescent. Flowers are of a yellow-greenish color and are grouped together to inflorescences called umbels. Dry fruits are designated squizocarps, they are broadly winged and ovoid in shape.

It is used in medicine for the treatment of renal and pulmonary conditions and to relieve toothache. It is important as forage, being consumed by sheep in spring and summer, particularly tender sprouts, flowers, and fruits.

Chamomile, whose scientific name is *Chamaemelum nobile* (L.) belongs to the Asteraceae (Compositae) family.

Wild chamomile is found in sandy-clayey soils and on the banks of water courses in Western and Southern Europe, North of Africa, Azores Islands and British Islands. It is naturalized in most of the Northeastern US states.

It has been used in traditional medicine since the XVIth century, and it is believed to have been grown in Rome since then because this plant does not grow spontaneously anywhere in Italy or along the French Mediterranean coastline. The English had probably used it since long before, and from England it passed on to Roman gardens and orchards. In Argentina its presence is official since the sixth edition of the Pharmacopoeia.

*Chamaemelum nobile* (L.) is a lively herbaceous species of the Asteraceae (Compositae) family. Its ramified stems may be decumbent, ascendant or erect. The plant reaches variable heights from 20 to 40 cm. It has alternate 2-3 pinnate leaves of a light green color; lower leaves are pedunculated, upper leaves are sessile. Flowers sit on conical receptacles, grouped in terminal solitary capitula, with central yellow tubular florets and peripheral white ligulet florets. The fruit is a very small achene without pappus, slightly flattened, of yellow-greenish color. Flowering is in spring and summer.

The single flower variety resembles a small daisy, but the valuable Roman chamomile has double flowers, most of them white.

The above described species corresponds to the single flower variety. The plants with double flowers have a higher value, and are characterized by capitula comprised only by white ligulate sterile flowers, their aspect resembling those of white clover heads.

It comprises dried floral capitula, of strong aromatic scent and bitter taste. The bitter taste is due to 0.6% germacranolides (i.e. cyclodecadiene lactones: nobiline and derivatives thereof).

Floral capitula contain from 0.4 to 0.9% essential oils, 8 to 10% water, 6 to 7% mineral elements, an alkaloid called anthemine, tannin, resin, a phytosterol, gum, calcium, etc.

The essential oil (not less than 0.4%) obtained from the dry floral heads contains monoterpene hydrocarbons, angelic acid, pinocarvons, pinocanphones, mirtenal, nerolidol, farnesal, beta-damascenone, lepalone, 4-hydroxibenzaldehyde, 3C4diol each sterified with isobutiric and angelic acid. In floral capitula there are also sesquiterpene lactones, nobiline, 3-epinobiline, 1,10-epo-xinobiline, 3-dehydronobiline, eucannabinolide, and hydroxyisonobiline; n-heptacosane, n-nonacosane; lignoceryl alcohol and hexacosanol; b-amirine, and taraxasterol and b-sitosterol; caffeic and ferulic acids, scopoletin, scopolosid, luteoline, kaempferol, apiine, apigenin, anthemonide, cosmeoside, and luteolin-7-glucoside.

Nobiline and its derivatives, sesquiterpene lactones, exhibit in vitro anti-tumoral activity against human tumor cells. The extracts combined with *Hammamelis virginiana* extracts and other constituents, are particularly appropriate for the protection of skin against contaminating agents. It has been reported to exhibit carminative, spasmolytic, sedative, anti-emetic, tonic, anti-phlogistic, diaphoretic, stomachic activities.

*Chamaemelum* may be used as a bitter aromatic, affecting the digestive system, and for dyspepsia, nausea, and vomits, anorexia, pregnancy vomits, and dysmenorrhea.

There are many Patents dealing with herbal formulations and/or compositions for the treatment of diseases, among others, diabetes (see U.S. Pat. Nos. 6,780,440; 6,770,307; 6,576,270; 6,551,627).

BRIEF DESCRIPTION OF THE INVENTION

It is an object of the present invention to provide a new herbal formulation for the treatment of diabetes, comprising the herbs *Mulinum spinosum* and *Chamaemelum nobile* mixed at a specific proportion using mineral water as a solvent.

Another object of the present invention is a herbal formulation comprising, in exemplary proportions, 0.85 grams of *Mulinum spinosum* and 0.15 of *Chamaemelum nobile* per liter and a half of mineral water, whereby preferably 10doses of infusion are obtained, although each dose may vary depending on the treatment and/or stages thereof.

It is a further object of the present invention to provide a method for obtaining a herbal formulation, preferably 10 doses of the same, comprising the steps of:

a) adding 0.85 grams of *Mulinum spinosum* and 0.15 of *Chamaemelum nobile* per liter and a half of water at 100° C. during 15 seconds, or to any desired volume provided the same proportions are maintained, b) allowing the mixture to stand until the herbs have settled, c) filtering the mixture, to obtain the desired solution.

DETAILED DESCRIPTION OF THE INVENTION

The present invention refers to a herbal composition in the form of an infusion. It may be prepared by adding 0.85 g of Neneo and 0.15 g of *Chamomile* in 1 liter and a half of mineral water to obtain preferably 10 doses comprising 150 cm$^3$ of infusion per dose. Of course, volume of doses may vary according to the treatment and/or stages thereof. The water utilized shows distinct characteristics as can be seen in the following biochemical analysis:

Determinations in water

| Bacteriological test | Aerobic bacterial count |
|---|---|
| Culture at 37° C., 24 hs, in Nutritional Agar: | 2 ufc/mL, with a threshold limit of 500 ufc/mL. |
| Coniform Bacteria (Wilson) | less than 2.4 NMP/100 mL, with a threshold limit less than or equal to 3. |
| Thermotolerant Coliforms (*E. coli*) | Absent, with a threshold limit of absence in 100 mL. |
| *Pseudomonas aeruginosa* | Absent, with a threshold limit of absence in 100 mL. |
| pH: | 7.55 |
| specific conductivity: | 60 umho/cm |
| Dissolved Salts (105° C.): | 45 mg/L |
| Turbidity: | Less than 1 NTU |
| Color: | 2.5 u.c. |

| Anions | mEq/L | mg/L |
|---|---|---|
| Alkalinity (CaCO3) | — | 22.5 |
| Carbonates ($CO_3^{2-}$) | — | 0 |
| Bicarbonates ($HCO_3^-$) | 0.45 | 27 |
| Chlorides ($Cl^-$) | 0.15 | 5 |
| Sulphates ($SO_4^-$) | — | less than 10 |
| Cations | mEq/L | mg/L |
| Hardness ($CaCO_3$) | — | 25 |
| Calcium ($Ca^{++}$) | 0.40 | 8 |
| Magnesium ($Mg^{++}$) | 0.10 | 1.2 |
| Sodium ($Na^+$) | 0.20 | 5 |
| Potassium ($K^+$) | — | less than 0.5 |
| | mEq/mL | mg/L |
| Organic matter | — | 15 |
| Nitrates ($NO^{3-}$) | — | 1.6 |
| Nitrites ($NO^{2-}$) | — | less than 0.05 |

| -continued | | |
|---|---|---|
| Phosphates ($PO_4^{3-}$) | — | less than 0.1 |
| Iron | — | less than 0.1 |
| Fluoride | — | less than 0.1 |
| Arsenic | — | less than 0.05 |

The research stage began in 1998 and 35 cases of diabetes were treated.

From 1998 to this date, more cases have been observed in men (55%) than in women and their age ranged from 35 to 73.

The treatment consisted in the daily administration of 150 cm$^3$ doses of infusion, gradually lowering the dose until it reached 50 cm.$^3$. The average period of treatment was of three months and all cases resulted in cure of the disease.

It is noted that the herbal composition of the present invention does not seem to produce side effects or adverse reactions and that clinical studies carried out as prescribed by the physicians allowed for a follow-up which showed a normalization of blood sugar levels.

What is claimed is:

1. A herbal formulation comprising:
    a mixture of *Mulinum spinosum, Chamaemelum nobile* and mineral water.
2. The herbal formulation of claim 1 wherein the formulation comprises:
    0.85 grams of *Mulinum spinosum;* and
    0.15 grams of *Chamaemelum nobile*
    in 1.5 liters of mineral water.
3. A method for obtaining the herbal formulation of claim 1, comprising the steps of:
    a) adding 0.85 grams of *Mulinum spinosum* and 0.15 grams of *Chamaemelum nobile* to 1.5 liters of mineral water at 100 C. for 15 seconds to form a mixture,;
    b) allowing the mixture to stand until the herbs have settled;
    c) filtering the mixture. to obtain a solution.

* * * * *